(12) United States Patent
Manders et al.

(10) Patent No.: US 12,599,348 B2
(45) Date of Patent: Apr. 14, 2026

(54) SPEED VARIABLE TDS OPERATION IN X-RAY IMAGING SYSTEMS

(71) Applicant: GE Precision Healthcare LLC, Wauwatosa, WI (US)

(72) Inventors: Adam Manders, Madison, WI (US); Michael R. Buchholz, McFarland, WI (US); James Wear, Madison, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 264 days.

(21) Appl. No.: 18/243,343

(22) Filed: Sep. 7, 2023

(65) Prior Publication Data

US 2025/0082288 A1 Mar. 13, 2025

(51) Int. Cl.
| | |
|---|---|
| *A61B 6/06* | (2006.01) |
| *A61B 6/00* | (2006.01) |
| *A61B 6/40* | (2024.01) |
| *A61B 6/42* | (2024.01) |
| *A61B 6/50* | (2024.01) |

(52) U.S. Cl.
CPC ............. *A61B 6/482* (2013.01); *A61B 6/4078* (2013.01); *A61B 6/4233* (2013.01); *A61B 6/505* (2013.01); *A61B 6/54* (2013.01)

(58) Field of Classification Search
CPC ......... A61B 6/482; A61B 6/486; A61B 6/488; A61B 6/505; A61B 6/5217; A61B 6/5264; A61B 6/544; A61B 6/545; A61B 6/588; A61B 5/4504; G06T 2207/30008
See application file for complete search history.

(56) References Cited

U.S. PATENT DOCUMENTS

2023/0136752 A1 5/2023 Wear et al.

FOREIGN PATENT DOCUMENTS

CN 116035600 A * 5/2023 ............. A61B 6/589

* cited by examiner

*Primary Examiner* — Don K Wong
(74) *Attorney, Agent, or Firm* — Boyle Fredrickson, S.C.

(57) ABSTRACT

TDS (Time-Delayed Summation) acquisition systems and methods may be used within various imaging device and systems, such as a densitometry system with highly pixelated 2-D detectors and compact x-ray fan beam that scans patients in a rastering pattern across the patient axis. An improved system and method is described for extending the usability of TDS data on each transverse sweep of the scan, by acquiring data when the scan speed is variable. In this method, the TDS shift strobe signal is no longer a constant periodic function. Instead the time between strobes is dependent on the scan velocity and the strobe sequence is generated to provide constant sampling distance between strobes. Thus, the TDS shift sequence insures a constant image pixel size, enabling undistorted images despite the variable speed occurring during the signal summation.

19 Claims, 13 Drawing Sheets

SPEED VARIABLE TDS OPERATION IN X-RAY IMAGING SYSTEMS

BACKGROUND OF THE DISCLOSURE

The subject matter disclosed herein relates generally to medical diagnostic imaging systems, and more particularly to a system and method for acquiring patient images for use in determining a patient body composition, a bone mineral density (BMD), and combinations thereof.

Dual-energy imaging systems such as a body composition system and/or bone densitometer includes an x-ray source that emits a collimated beam of dual-energy x-rays to image a patient. An x-ray detector is positioned with respect to the x-ray source to receive the x-rays passing through the patient. The x-ray detector produces electrical signals in response to the received x-rays. The electrical signals are converted to digital signals that are utilized by the imaging system to generate images of the patient.

Measurements of the x-ray absorption by an object at two different x-ray energies can reveal information about the composition of that object as decomposed into two selected basis materials. In the medical area, the selected basis materials are frequently bone and soft tissue. The ability to distinguish bone from surrounding soft tissue allows x-ray images to yield quantitative information about in vivo body composition and/or bone density for the diagnosis of osteoporosis and other bone disease.

Current bone densitometers use frame-based data acquisition methods to scan patients. In this mode the use of highly-pixellated 2-D detectors generates large volumes of data with typically low x-ray statistics per pixel that complicates image reconstruction. Therefore, there is a need for an improved system and method to acquire body composition and/or bone density information.

TDI (Time-Delayed Integration) is well known in scanning applications as a means to improve x-ray statistics per pixel in 2-D x-ray detectors. Detector pixels integrate charge from absorbed x-rays during short time intervals and store it in charge storage wells on solid state ASICs. Each pixel's collected charge is shifted to neighboring pixel's storage well in synchronization with the beam motion, such that a feature in the scanned object remains on an x-ray line between a single point in the detection plane and source's focal spot. At the end of the row of pixels, charge collection corresponding to that point is complete, digitization of the integrated charge is performed and ultimately transferred to computing devices for image calculation.

A similar method called TDS (Time-Delayed Summation) or DTDI (Digital TDI) performs x-ray (or photon) counting rather than charge integration. TDS has each detector pixel measures charge from absorbed x-rays and immediately discriminate them into different energy windows (e.g. Low and High energy windows) during short time intervals. This pixel's x-ray count is incremented for the appropriate energy window in ASIC memory. The incremented sums of x-rays are shifted to a neighboring pixel's memory register in synchronization with the beam motion, such that a feature in the scanned object remains on an x-ray line between a single point in the detection plane and source's focal spot.

In both TDI and TDS methods, this shifting synchronization is dependent on the feature's magnification, detector pixel pitch and scan speed. In conventional applications the scan speed and shift frequency are constant and each image pixel's dimension in the scan direction is therefore also constant. In the detector plane, this dimension is usually equal to the detector pixel width. After readout the image data consists of contiguous columns or "lines" of image pixels with uniform size and count summing time. This is desirable for ease in analysis since beam intensity comparisons between pixels and image formation are straightforward.

Transverse scanning in DXA utilizes raster scanning across the patient axis and necessarily requires rapid acceleration and deceleration of the x-ray source to the constant scanning speed. Current body composition systems, densitometers and TDS techniques only acquire data while the x-ray source is travelling at constant speed. Not acquiring data during acceleration and/or deceleration phases results in unused dose to patients, so the common approach minimizes motion ramp time. This approach implies operating at the highest feasible accelerations and is ultimately limited by the finite motion motor torque. Furthermore, faster acceleration and deceleration times are more likely to introduce undesirable mechanical vibration in the scanner arm that degrades image quality or else requires additional traveling distance to ensure dampened vibration before imaging the region-of-interest.

As a result, it is desirable to develop a system and method for capturing data during periods of acceleration and deceleration of the x-ray source that does not require extreme speeds during the acceleration and deceleration phases of the scanning device/x-ray source. Further, the ability to capture and use data within the variable speed regions would enable less wasted dose to the patient and shorter scan times since transverse travel distance could be reduced.

BRIEF DESCRIPTION OF THE DISCLOSURE

The invention recognizes that TDS (Time-Delayed Summation) acquisition methods may be used within a body composition and/or densitometry system with highly pixelated 2-D detectors and compact x-ray fan beam that scans patients in a rastering pattern across the patient axis. A method is described for extending the usability of TDS data on each transverse sweep of the scan, by acquiring data when the scan speed is variable. In this method, the TDS shift strobe signal is no longer a constant periodic function. Instead the time between strobes is dependent on the scan velocity and the strobe sequence is generated to provide constant sampling distance between strobes. Thus the TDS shift sequence insures a constant image pixel size, enabling undistorted images despite the variable speed occurring during the signal summation.

In standard, constant-speed TDS operation, a constant time of signal summation occurs between each shift. This implies there is no need for time-elapsed normalization between image pixels, so signal intensity between each image pixel may be directly compared. With variable-speed TDS, this assumption is no longer valid and the time elapsed during the entire shift sequence must be recorded for each line of image pixels. The inverse of this time integral is then used to normalize the signal of all image pixels. TDS shift strobes are generated by a motion controller that coordinates scan motion and issues each strobe to insure a constant distance was travelled during that sampling time. This motion controller may calculate distance travelled according to predetermined motion program or sequence. Alternatively, the controller can estimate distance travelled by monitoring motion-encoded signals from the motor and/or motion controller providing motion of the x-ray source. Concurrently, the data acquisition controller which is performing the TDS operation records the time elapsed during the entire shift sequence for an image pixel. Prior to image generation, the raw signal summation for each pixel must be normalized by the elapsed time and corrected for any acquisition deadtime. At this point, image generation and quantitative signal analysis can proceed as in the constant-speed TDS operation.

One additional advantage of variable-speed TDS operation in DXA occurs when significant portions of a raster scan is spent in the acceleration (and deceleration) of the source/detector along the transverse path. For faster scan speeds, particularly those used for whole body DXA scanning, the distance required for acceleration is larger since translation motors have finite power and torque. Without incorporating data from the acceleration regions, the scan field must necessary be expanded, resulting in longer scan times. For whole body scanning, where the entire width of the body must be scanned, this ramping buffer necessarily requires a wider patient table, which adds expense and technical design challenges to the gantry. Ultimately the additional buffer requirement limits the maximum transverse scan speed and therefore the minimum scan time. Lowering scan times is an important goal since it improves patient comfort, improves scan quality due to reduced chance for patient motion, and increases overall patient throughput of the scanning facility.

To reduce the ramping buffer width, current implementations will ramp at the motor's maximum acceleration, which impacts the maximum impulse to the scanner arm. This can lead to undesirable jerks and vibrations that may degrade image quality and quantitative measurements. Using the data within the ramp region enables smoother acceleration profiles or programs, which take longer than a constant, maximal acceleration to achieve the maximum scan speed. Smoother profiles will impart lower impulses to the scanner arm, leading to reduced jerk and potentially lower vibration.

Another advantage of variable-speed TDS operation is that it enables TDS operation in conditions where adjusting scan velocity in response to external signal intensity is desirable. For example, decreases in signal intensity occur when scanning denser regions, meriting a dynamic lowering of scan speeds to increase the x-ray statistics per image pixel. Conversely, when signal intensity is high, increasing scan speed would reduce patient dose without a relative compromise to the statistical quality of image pixels.

In accordance with an embodiment of the present technique, an imaging device includes an X-ray source operative to transmit X-rays through an object, wherein the X-ray source is collimated to produce a diverging beam of radiation, a detector operative to receive the X-ray energy of the X-rays after having passed through the object, a processing system operably connected to the X-ray source and the detector, the processing system programmed to control movement of the X-ray source and the detector relative to the object, and to perform a time delayed summation (TDS) process to generate images from the X-ray energy received by the detector, and an electronic memory operably connected to the processing system and storing instructions for the operation of the processing system in performing imaging procedures, wherein the processing system is configured to determine a time delayed summation (TDS) shift frequency that varies with speed of the X-ray source and detector and to perform a scan of the object based on the speed-variable TDS shift frequency.

In accordance with another embodiment of the present technique, a method for performing a time delayed summation (TDS) in an imaging procedure for an object includes the steps of providing an imaging device having an X-ray source operative to transmit X-rays through an object, wherein the X-ray source is collimated to produce a diverging beam of radiation, a detector operative to receive the X-ray energy of the X-rays after having passed through the object, a processing system operably connected to the X-ray source and the detector, the processing system programmed to control movement of the X-ray source and the detector relative to the object, and to perform a time delayed summation (TDS) process to generate images from the X-ray energy received by the detector, and an electronic memory operably connected to the processing system and storing instructions for the operation of the processing system in performing imaging procedures, determining a time delayed summation (TDS) shift frequency that varies with speed of the X-ray source and detector, performing a scan of the object based on the speed-variable TDS shift frequency, and generating an image of the object based on detected X-ray energy signals at the detector based on the scan.

In accordance with yet another embodiment of the present technique, a medical imaging system having a multi-energy X-ray source operative to transmit X-rays through a patient is provided. The X-ray source is collimated to produce a diverging beam of radiation. The medical imaging system further includes a detector operative to receive the X-ray energy of the X-rays after having passed through the patient and a processing system. The detector includes detector pixels arranged in at least one row. The processing system is programmed to perform a scan of the patient based on a speed-variable time delay summation (TDS) frequency and to generate at least two images of a patient bone corresponding to the multi-energy levels of the multi-energy X-ray source. The processing system is further programmed to determine at least one of a patient body composition, a bone mineral density (BMD), and combinations thereof, based on the at least two images.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE DISCLOSURE

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Exemplary embodiments of dual-energy x-ray systems and methods for acquiring, for example bone and tissue information are described in detail below. In particular, a detailed description of an exemplary dual-energy x-ray system will first be provided followed by a detailed description of various embodiments of methods and systems for generating patient anatomy images that may be used to diagnose a medical condition such as osteoporosis for example. In one embodiment, the system and method may be used for acquiring and measuring bone mineral density, bone tissue information, and other bone related information from patient bone images. In another embodiment, the system and method may be used for determining body composition which distinguishes lean and fat tissue in regions which do not contain bone.

At least one technical effect of the various embodiments of the systems and methods described herein is to acquire accurate patient anatomy such as bone images using a dual-energy x-ray imaging system. In some embodiments, a single dual-energy x-ray scan, and more particularly, a single body scan is used to acquire image information for a number of different bones, from which bone lengths are determined.

Figure 1:
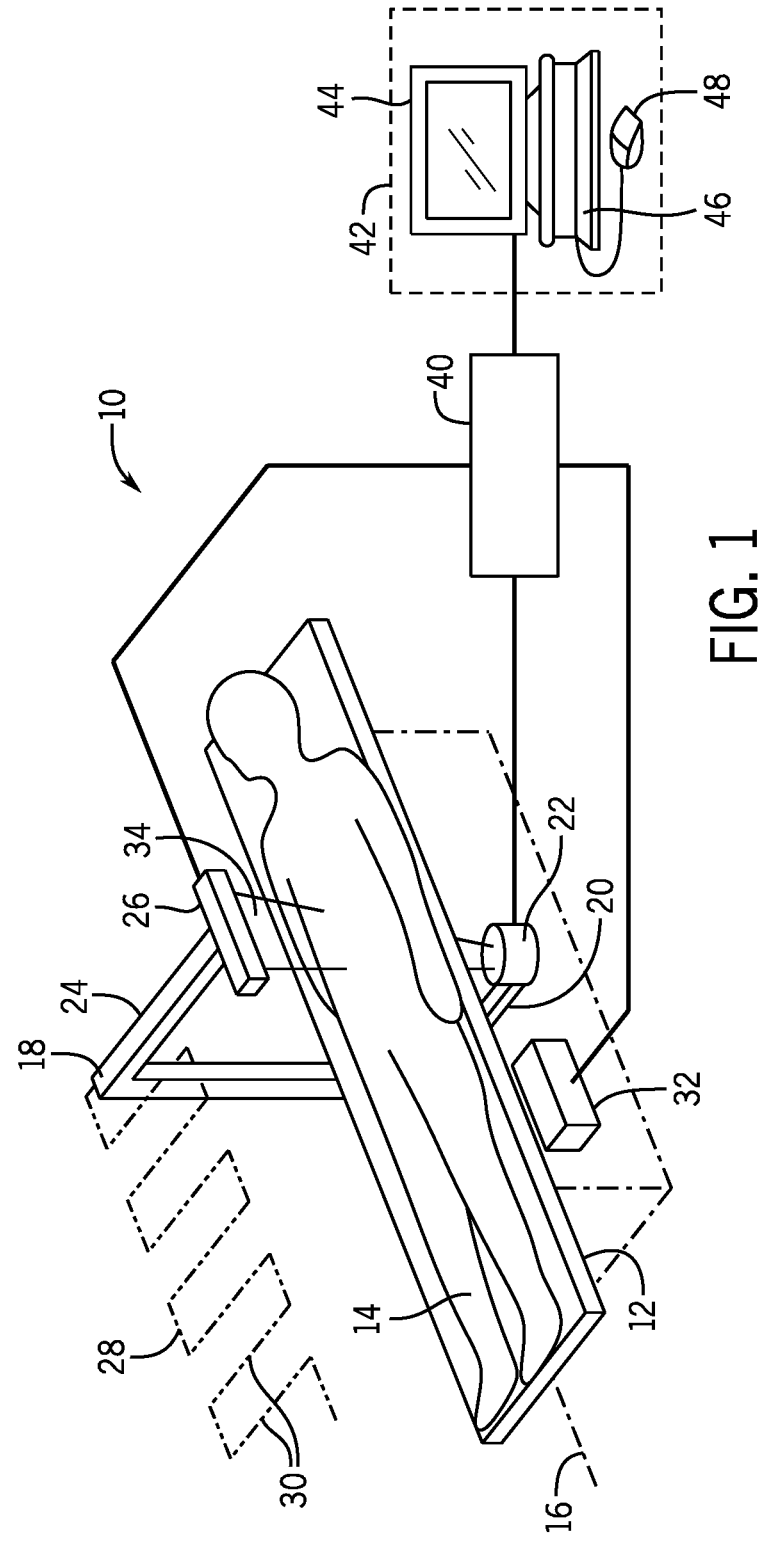
FIG. 1 is a schematic diagram of a dual-energy x-ray imaging system illustrating a full body scan, in accordance with an embodiment of the present technique.

FIG. 1 is a schematic diagram of an exemplary dual-energy x-ray device or system, illustrated as a dual x-ray absorptiometry (DEXA or DXA) device or system 10, such as that disclosed in Wear et al. US Patent Application Publication No. US2023/0136752, entitled System and Method For Imaging A Subject, the entirety of which is expressly incorporated herein by reference for all purposes, which is also referred to as dual energy bone densitometer system capable of performing bone densitometry. The device or system 10 constructed in accordance with various embodiments is configured to measure at least an area of a bone, a length of a bone, a bone mineral content (BMC), a bone mineral density (BMD), and a tissue thickness or density. The BMD is calculated by dividing the BMC by the area of the bone. During operation, an x-ray beam with broadband energy levels is utilized to scan a subject, for example, to scan a human subject to image the bones of the human subject. The acquired images of the bones are used to diagnose a medical condition such as osteoporosis. The images may be generated in part from determined bone density information acquired during a dual-energy x-ray scan.

The device or system 10 includes a patient table 12 providing a horizontal surface for supporting a subject, for example, a patient 14 in a supine or lateral position along a longitudinal axis 16. The system 10 also includes a support member, for example, a C-arm 18. The C-arm 18 has a lower end 20 that is positioned beneath the patient table 12 to support an x-ray source 22. The C-arm 18 has an upper end 24 that is positioned above the patient table 12 supporting an x-ray detector 26. Optionally, the x-ray detector may be coupled to the lower end 20 and the x-ray source 22 coupled to the upper end 24. The x-ray detector 26 may be fabricated, for example, as a multi-element or pixelated cadmium-tellurium (CdTe) detector providing for energy discrimination. The x-ray source 22 and the x-ray detector 26 may be moved in a raster pattern 28 so as to trace a series of transverse scans 30 of the patient 14 during which dual energy x-ray data is collected by the x-ray detector 26. The transverse scanning procedure generates either a single image or quantitative data set, from a plurality of scan images acquired across a patient, wherein the x-ray source 22 and the detector 26 are either longitudinally aligned with the superior-inferior axis of the patient or transversely from the patient's left to right. Scanning a patient using a transverse motion facilitates minimizing the time between acquisitions of adjacent scan images because the transverse direction across the patient is shorter than the longitudinal direction across the patient. Thus, transverse scanning can reduce the severity of patient motion artifacts between scan images allowing the images to be more accurately merged.

The transverse scanning motion is produced by actuators and/or a motor 35 operably connected to the C-arm 18 and under control of a motion or translation controller 32. During operation, the x-ray source 22 produces a fan beam 34 having a plane that is parallel to the longitudinal axis 16. Optionally, the fan beam 34 may have a plane that is perpendicular to the longitudinal axis 16. The raster pattern 28 is adjusted such that there is some overlap (e.g., slight overlap of 10 percent) between successive scan lines of the fan beam 34. The x-ray source 22, the x-ray detector 26, and the motion or translation controller 32 communicate with, and are under the control of, a computer 40 which may include both dedicated circuitry and one or more processors having the ability to execute a stored program, such as stored within an electronic memory 41 operably connected to the computer 40.

Referring again to FIG. 1, the computer 40 communicates with a terminal 42 including a display 44, a keyboard 46, and a cursor control device such as a mouse 48 allowing for operator input and the output of text and images to the operator. In some embodiments, the computer 40 is located remotely from the workstation 42. Optionally, the computer 40 may form a portion of the workstation 42. The computer is adapted to perform one or more processing operations. The acquired bone and tissue information, for example, image and density information may be processed and displayed in real-time during a scanning session as the data is received. Additionally or alternatively, the data may be stored temporarily in a memory device on the computer 40 during a scanning session and then processed and displayed in an off-line operation. The information may also be stored in a long-term storage device (e.g., hard-drive or server) for later access, such as during a follow-up scan of the same patient and useful to monitor, for example, the change in bone and tissue density over a period of time. The display 44 includes one or more monitors that present patient information, including the scanned image and the bone length images to the operator for diagnosis and analysis. The displayed images may be modified and the display settings of the display 44 also manually adjusted using the keyboard 46, the mouse 48, or a touch screen icon on the display itself.

During operation, the device or system 10 is configured to operate in either a dual energy x-ray mode or a single energy x-ray mode. In the single energy mode, the x-ray source 22 emits x-rays at a narrow band of energies of a few keV and in the diagnostic imaging range of approximately 20-150 keV. In the dual-energy mode, the x-ray source 22 emits radiation at two or more bands of energy emitted simultaneously or in rapid succession. The x-ray source 22 may also be configured to emit a single broadband energy of more than a few keV over the diagnostic imaging range. The system 10 may be switched between the dual energy mode and the single energy mode by increasing or decreasing the x-ray source 22 voltage and/or current. The system may also be switched between the dual energy mode and the single energy mode by removing or adding a K-edge filter. It should be noted that the x-ray source 22 may emit x-rays at different energies or ranges of energies.

The x-ray source 22 may be configured to output a fan beam of x-rays 34 as shown in FIG. 1. In some embodiments, the computer 40 controls the system 10 to operate in the single energy mode or dual-energy mode to determine the bone or tissue information of at least some of the scanned body. The single energy mode generally enables higher resolution images to be generated. The acquired images may then be used to measure, for example, bone density or other bone and tissue characteristics or content. As discussed above, the dual-energy x-ray scan may be a rectilinear scan of the entire patient body, which may be performed in a transverse-type scanning sequence as described above. During the dual-energy x-ray scan an image of the entire body of the patient may be acquired, which includes image information relating to the bones and tissue in the body. The full body or total body scan of the entire body may be performed as a single scanning operation, which may be a low dose mode scan. In some embodiments, instead of a full body or total body scan, individual rectangular regions of the body may be performed, which may be single sweep scans. Once the scan of the patient, or a portion thereof, is completed, the dual energy signals provided by the detector 26 are deconstructed into images of two basis materials, such as bone and soft tissue. The high and low energy signals can also be combined to provide a single energy mode having superior signal to noise ratio for imaging purposes.

The detector 26 shown in FIG. 1 may be embodied as either a linear array of detector elements, a side linear array of detector elements or pixels, which includes two transversely separated rows of detector elements, or a stacked array detector in which the detector elements are stacked along a direction of propagation of the radiation and are selectively sensitive to low and high energy spectrums, respectively.

Figure 2:
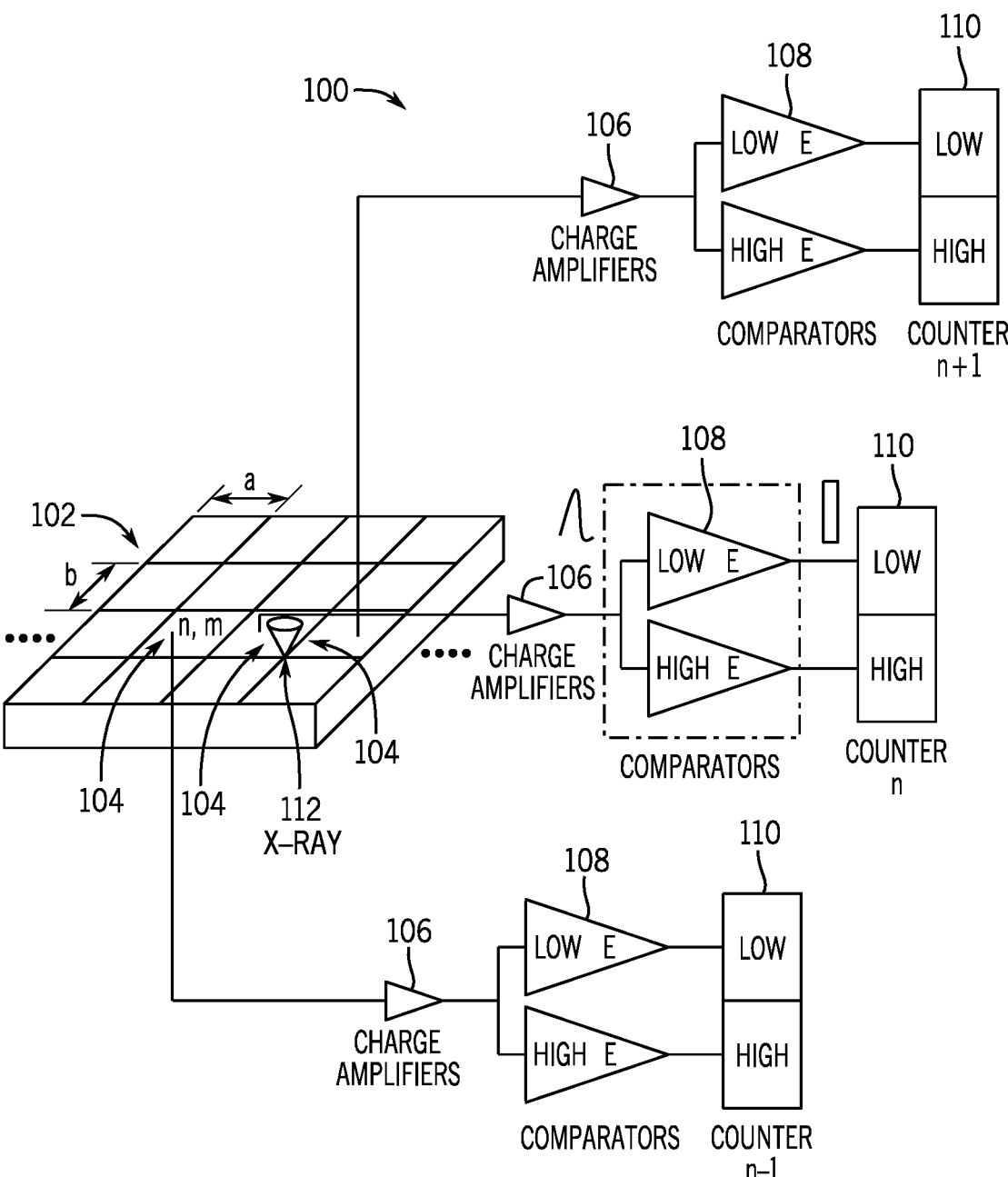
FIG. 2 is a schematic diagram of a detector and related circuitry used in FIG. 1, in accordance with an embodiment of the present technique.

FIG. 2 depicts a schematic diagram 100 of a detector and related circuitry used in system of FIG. 1. In general, schematic diagram 100 shows a detector 102 which can be used as detector 26 of FIG. 1. The detector 102 includes an array of detector pixels 104 having n rows and m columns. Each of these detector pixels are connected to a charge amplifier 106, one or more comparators 108 and a counter 110. When the x-ray beam 112, after passing through a subject or the patient, hits a particular detector pixel (e.g., pixel (n, m)), the detector pixel (n, m) converts the x-ray energy into a charge which is amplified by a charge amplifier 106. It should be noted that if the x-ray beam hits a border of the two detector pixels, two detector pixels may receive the x-ray energy which will be converted into two charges. Output of charge amplifier 106 is passed on to the comparator 108, which discriminate the charge into different energy windows (e.g. Low and High energy windows) and provides the corresponding output to the counter 110. The counter 110 then updates (increments) the corresponding low energy or high energy count based on the output from the comparator 108. The contents (or x-ray energy count) of the counter 110 are generally stored in a memory register of the corresponding detector pixel. It should be noted that if there is no charge from the x-ray detector pixel i.e., when no x-ray beam falls on the detector pixel, the counter 110 will not get updated. After a certain time duration (e.g., a recording period time duration), the x-ray energy count of the counter 110 are provided to a processor such as computer 40. Based on the number of counts from multiple counters, the processor finally determines the patient image which may be a bone image or a patient tissue image.

Figure 3:
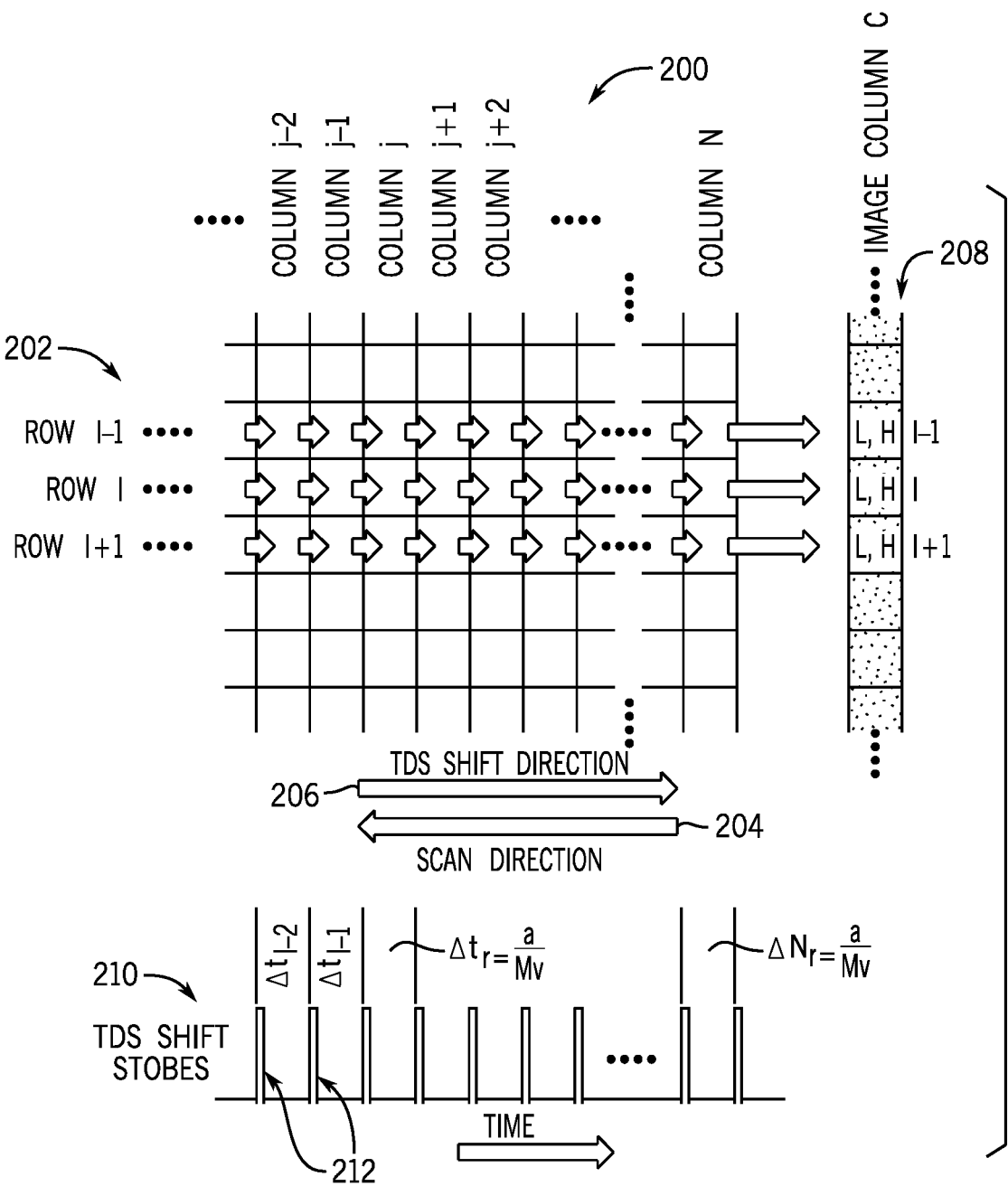
FIG. 3 is a schematic diagram of a prior art Time-Delayed Summation (TDS) technique.

In the present technique, a Time-Delayed Summation (TDS) technique is used instead of the embodiment shown in FIG. 2. The TDS technique is a process of adding together multiple exposures of the same object as it passes a detector. TDS technique allows images to be taken of moving objects. In the TDS technique, the incremented sums of x-ray energy counts are shifted to a neighboring detector pixel's memory register in synchronization with the x-ray beam motion, such that an object (e.g., a bone) in the scanned subject (e.g., a patient) remains on an x-ray line between a single point in the detector plane and source's focal spot. In the TDS method, this shifting synchronization is dependent on the object's magnification, detector pixel pitch and scan speed. Notably, objects at heights other than the optimum for time-delay synchronization will be blurred since signals through that object will be distributed across multiple points in the detector plane FIG. 3 is a schematic diagram 200 that describes the TDS method in accordance with an embodiment of the present technique. The schematic diagram 200 shows a detector 202 having a detector pixel array of n rows and m columns. As against FIG. 2, where after the recording period time duration, the x-ray energy count of a detector pixel counter is provided to a processor 40, in FIG. 3, the x-ray energy count of the detector pixel counter is shifted to a neighboring detector pixel counter after a TDS shift time duration. For example, in one embodiment, TDS shift time duration may be 0.56 msec and total number of shifts may be 60 for one acquisition whereas the recording period time duration in FIG. 2 may be 6 msec i.e., the recording period time duration may be longer than the TDS shift time duration. The shifting of x-ray energy count from one counter to the next is done for all the detector pixel counters in synchronization with the x-ray beam motion.

For example, if the x-ray scanner is sweeping across the patient and if the scan direction 204 of the x-ray beam is from right to left then the x-ray energy count shift direction 206 is from left to right i.e., opposite the scan direction. A pulse diagram 210 at the bottom of FIG. 3 shows TDS shift strobes or pulses 212 which have a TDS shift frequency f. The TDS shift frequency f translates into a TDS shift time duration $\Delta t_0 = 1/f$ between two pulses. Thus, whenever a TDS shift pulse is received, the counter contents of corresponding detector pixels are shifted to the neighboring counter. As an example, if the TDS shift time duration between two pulses 212 is 1 millisecond (f=1 khz) then the contents of the counter of detector pixel (i, j) are shifted to the right counter of detector pixel (i, j+1) after every 1 millisecond, where i and j corresponds to row number and column number respectively. In other words, the contents of all detector pixel counters corresponding to row i are shifted to their corresponding right column. Moreover, the contents of the last column N are shifted to a main detector memory buffer 208 and then finally to a processor for generating image of the object. In general, by shifting the contents of the counter to the neighboring counter and then adding them together, multiple x-rays passing through a bone of the patient are integrated as the x-ray beam passes through that bone over a given time duration. The TDS shift frequency f depends on a plurality of parameters such as a velocity v of the x-ray source motion and will be explained in more detail in subsequent paragraphs.

Figure 4:
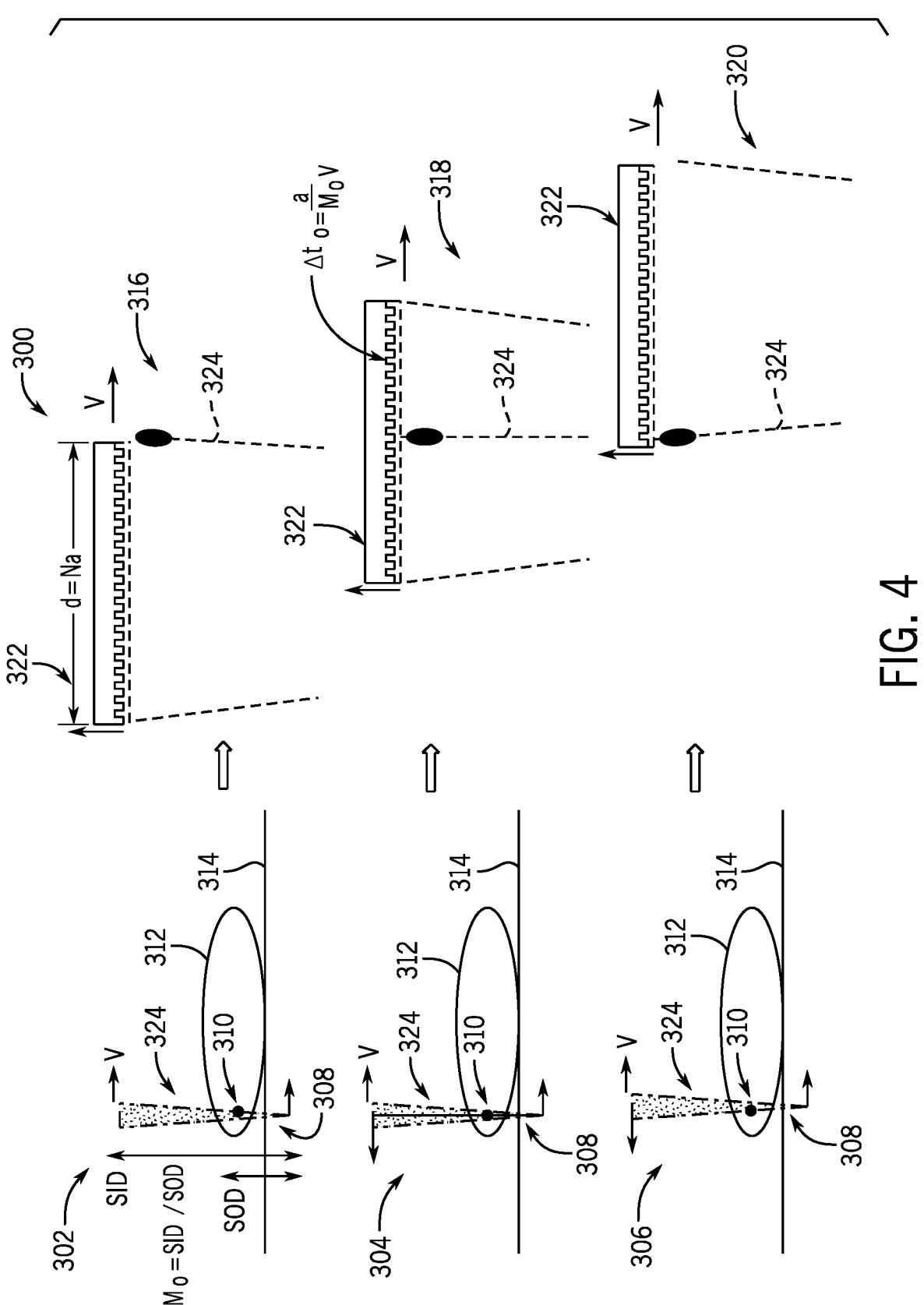
FIG. 4 is a schematic diagram depicting a TDS imaging sequence of a bone of a patient, in accordance with an embodiment of the present technique.

FIG. 4 is a schematic diagram 300 depicting TDS imaging sequence of a bone of a patient. Schematic diagram 300 shows three steps 302, 304, 306 of TDS imaging sequence corresponding to 3 positions of the X-ray beam 308 at three different time instances. Schematic diagram 300 shows an object e.g., a bone 310 in a patient 312 who is lying on a table 314. For all three steps 302, 304, 306, corresponding positions 316, 318, 320 of detector 322 are also shown in schematic diagram 300. The detector 322 includes N number of detector pixel columns, each pixel having dimension a. Because of the synchronization of speed and TDS shifting, the total detector width d remains a although the signal integrated by this pixel is received from a region of width Na.

When the x-ray scanner is sweeping across the patient, step 302 is the first time instance when the x-ray beam 308 passes through the bone 310. In the embodiment shown, the x-ray scanner is moving from left side to the right side in reference to the bone 310 at a velocity v. Thus, at step 302, the ray of the x-ray beam 308 passing through bone 310 is at an acute angle with respect to table plane 314 to start with. The attenuated x-ray beam 324 i.e., the x-ray beam 308 after passing through the bone 310 then hits the first detector pixel of the detector 322 as seen in detector position 316. Step 304 refers to a second time instance when the ray of the x-ray beam 308 passing through bone 310 is at a right angle with respect to table plane 314. The attenuated x-ray beam 324 then hits the middle detector pixel of the detector 322 as seen in detector position 318. Step 306 corresponds to a third time instance when ray of the x-ray beam 308 passing through bone 310 is at an obtuse angle with respect to table plane 314. In this instance, the attenuated x-ray beam 324 hits the last detector pixel as seen in detector position 320.

If the TDS method is not used then the charge accumulated at detector pixels corresponding to bone imaging at positions 316, 318 and 320 would remain at the same detector pixels i.e., first, middle and last detector pixel. This would result in bone image being distributed across the whole detector and so the final bone image would be blurry. Alternatively, the frame rate could be increased to reduce blurring, at the cost of increasing data volume and re-registration of frame in image reconstruction. However, in the TDS method, the contents of detector pixels are continuously shifted to the neighboring pixel counter at a TDS shift frequency till the bone is completely imaged and finally the charge corresponding to bone image at positions 316, 318 and 320 gets accumulated in a last detector pixel. The contents of the last detector pixels are then read out by the processor for generating the bone image. In other words, bone image charge at all the detector positions gets integrated in one detector pixel instead of getting distributed across the entire detector resulting in a less-blurry or clearer image of the bone.

In one exemplary embodiment illustrated in FIG. 4 of the case of TDS imaging a feature on the object plane, SOD, the TDS shift frequency is selected according to the formula:

$$f = \frac{M_0 v}{a} = \frac{1}{\Delta t}$$

where v is the constant scanning speed achieved after completing acceleration at the start of a sweep, a is the detector pixel dimension in the shift direction, and $M_0$ is the magnification of the object plane or object, i.e., bone. The magnification factor $M_0$ depends on the distance of the bone away from the source. At this optimal TDS frequency, a scanned feature in the object plane remains on an x-ray line between a single point in the detection plane and source's focal spot. In the image 302, the scanning fanbeam is being to be occluded by the feature in object plane SOD, projecting its image on the right most pixel in the detector array. In the image 304, detector scanning to the left has proceeded to where the feature is in the center of the fanbeam and its image is projected to the central pixel of the detector. Between these two points in time, the contents of all memory registers are shifting to the left every time interval, $\Delta t$, at the same speed as the feature's image, while the detector and beam move rightward. This results in the feature's "shadow" being tracked synchronously across the face of the detector. By the time the fanbeam has passed completely over the feature, as in the image 306, x-rays corresponding to the feature have been summed almost exclusively into a single image pixel. The memory register of the last exposed pixel in the detector contains the fully summed Low and High energy counts of the feature's image from all N pixels in the detector, but only the region, $a/M_0$, was imaged. One feature of TDS is that the signal within the image pixel builds up due to the shifting summation of counts.

Figure 5:
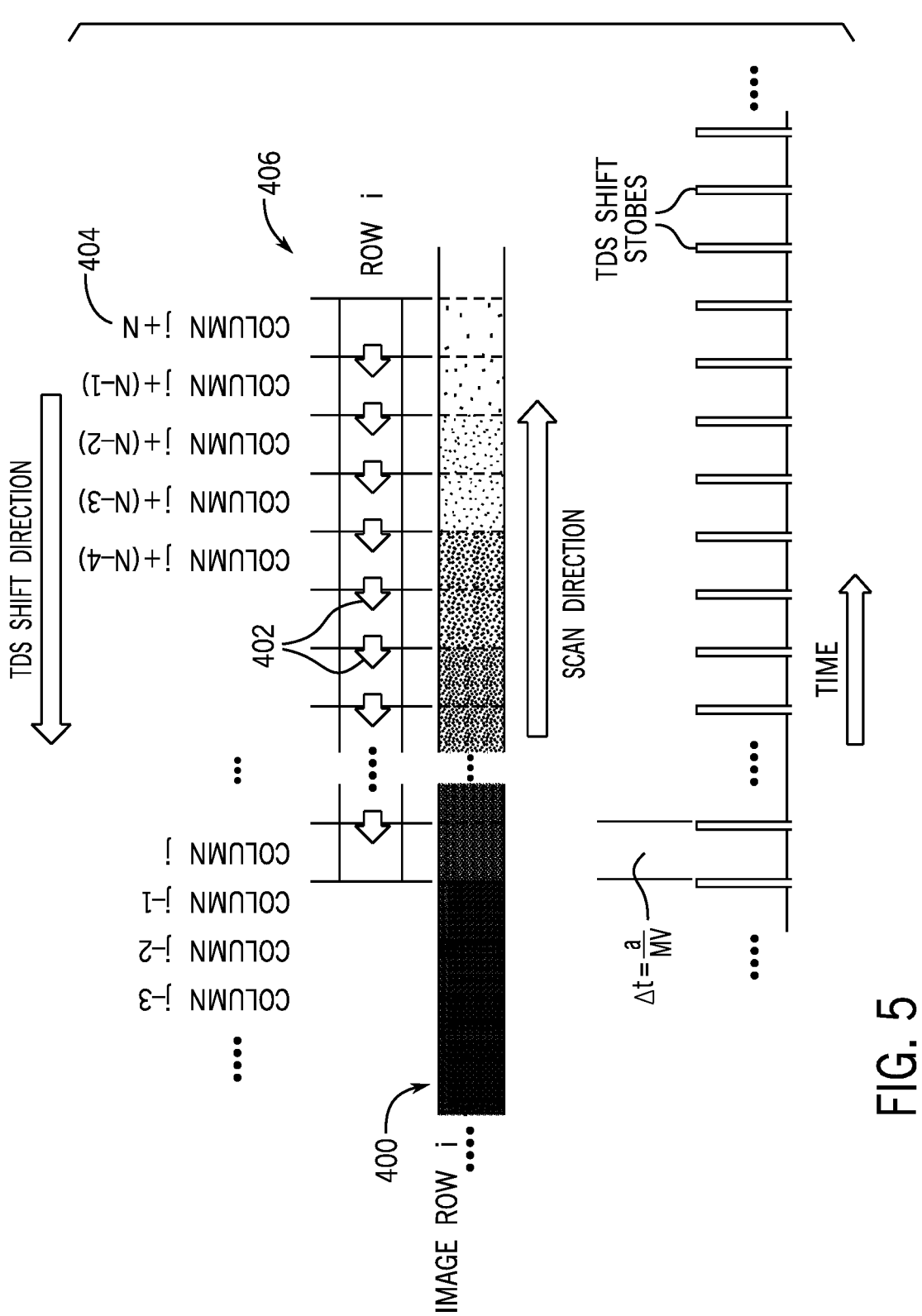
FIG. 5 is a schematic diagram depicting the x-ray count in the image pixel 400 increases with each shift when illuminated with a constant intensity beam in a prior art TDS imaging sequence effect of variable speeds on prior art TDS imaging procedures, in accordance with an embodiment of the present technique.

FIG. 5 shows in manner similar to FIG. 3 how the x-ray count in the image pixel 400 increases with each shift 402 when illuminated with a constant intensity beam. By the last, $N^{th}$, column 404 of the detector 406, the image pixel 400 has its final amplitude. Since there is constant beam intensity and time sampling, all image pixels 400 in the middle of a flat-field scan would have identical amplitude.

As described previously, transverse scanning utilizes raster scanning across the patient axis, each sweep across the patient generates an independent image. In the case of DXA, this image is of bone. Quantification of bone mineral density is performed through basis-set decomposition, which is well-known in literature and prior art. It relies on the mapping of the intensity of low-energy (LE) and high-energy (HE) portions of the x-ray beam to calibration surface fits of LE and HE x-ray counts taken through basis-set materials at pre-determined beam intensities. Therefore it is critical that detector pixel size and sampling time are well known and signals reliably scaled. In standard implementation of bone densitometers with one- or two-dimensional detector arrays, frames of data are only acquired during the constant-speed portions of the transverse scan. Each pixel of the detector independently and simultaneously counts the incident LE and HE x-rays for a constant sampling time, which due to the constant speed of motion of the source 22 and the detector 26 corresponds to a regular and constant pixel area being swept out for each image pixel. These regular frames of data are transferred to a controlling computer 40 for image reconstruction and analysis to derive bone mineral density or other appropriately calibrated materials. However, in these prior art TDS scanning methods described previously, within the acceleration/deceleration ramping region data is discarded or never acquired at all. To limit the width of this ignored ramping zone, in the prior art the acceleration is constant and maximized to achieve the desired constant scanning speed for the source 22 and detector 26 as quickly as possible. Usually the maximum acceleration is limited by the torque capability of the motor and/or the mechanical constraints of the structure of the source 22 and detector 26 to minimize vibrations, thus creating the need to extend scan paths or lengths to accommodate for the acceleration and deceleration/ramping zones.

Figure 6:
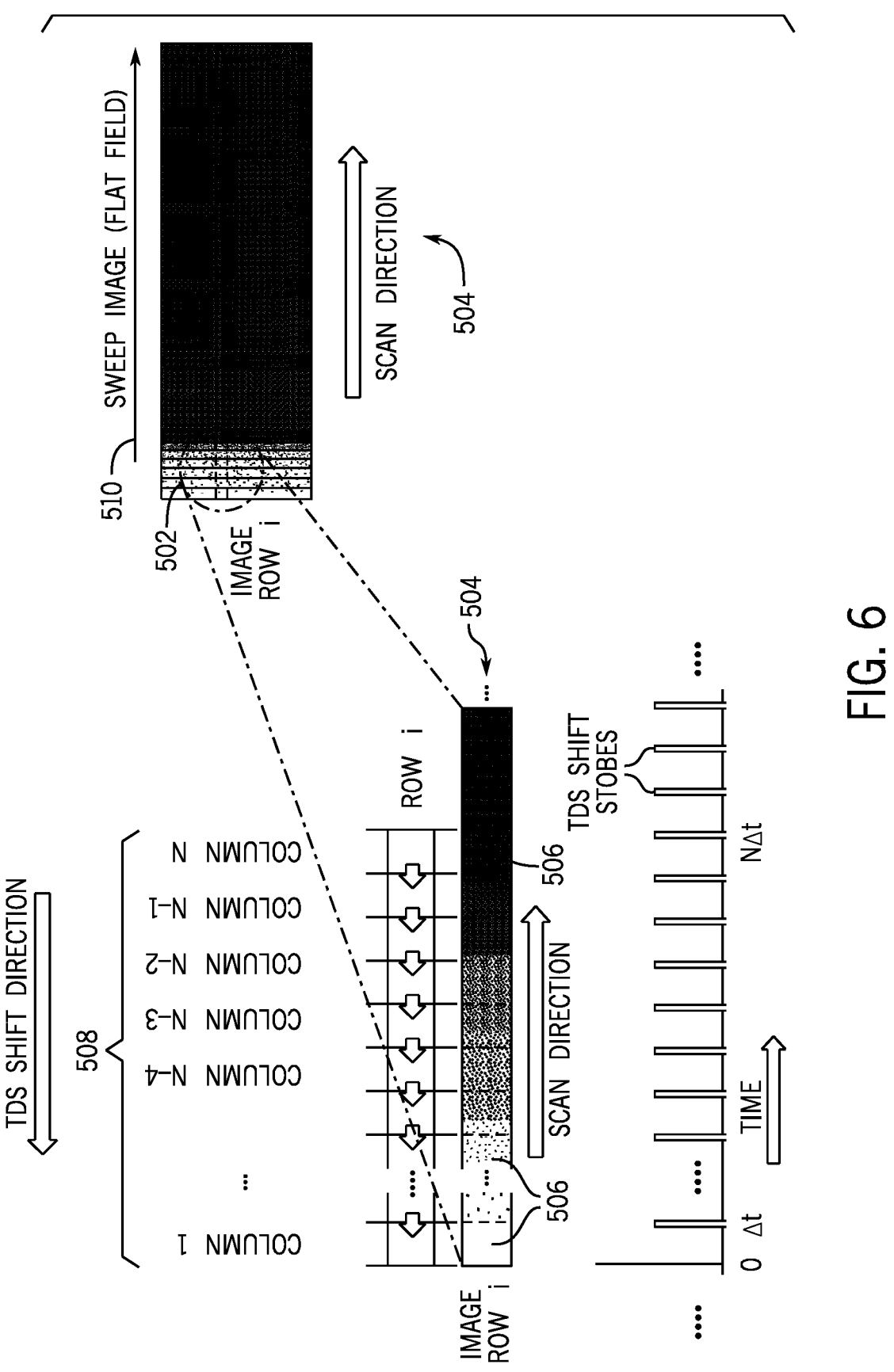
FIG. 6 is a schematic diagram depicting the effect of variable source speeds on prior art TDS imaging procedures.

As a result of these ramping periods or zones 502, at the very beginning of a scan sweep 504, the summation is zero (or unknown) initially in all pixels and the first N image pixels 506 will only have the partial summation of beam-induced signal before its detector pixels sum is shifted to memory, with the case of this initial build-up in the first columns 508 of a sweep illustrated in FIG. 6. These first N columns 508 must be discarded because of their unknown previous contents. In conventional transverse scanning, only data is collected or kept when the source 22 and detector 26 are travelling at constant scan speed/within constant speed zone 510, since the distance per time-sample is non-uniform outside of the constant scan speed zone 510. With prior art TDS, an additional N columns 508, which may be the same or different in number than the columns 508 in the ramp zone 506, must also be discarded once constant speed is attained/the constant speed zone 510 is reached, due to the inclusion of summations during the earlier, ramping period 502. At low scan speeds this unusable region of the scan 504 is acceptably small, but at high speeds with constrained acceleration this may become a significant fraction of the overall distance of the scan sweep 504.

Figure 7:
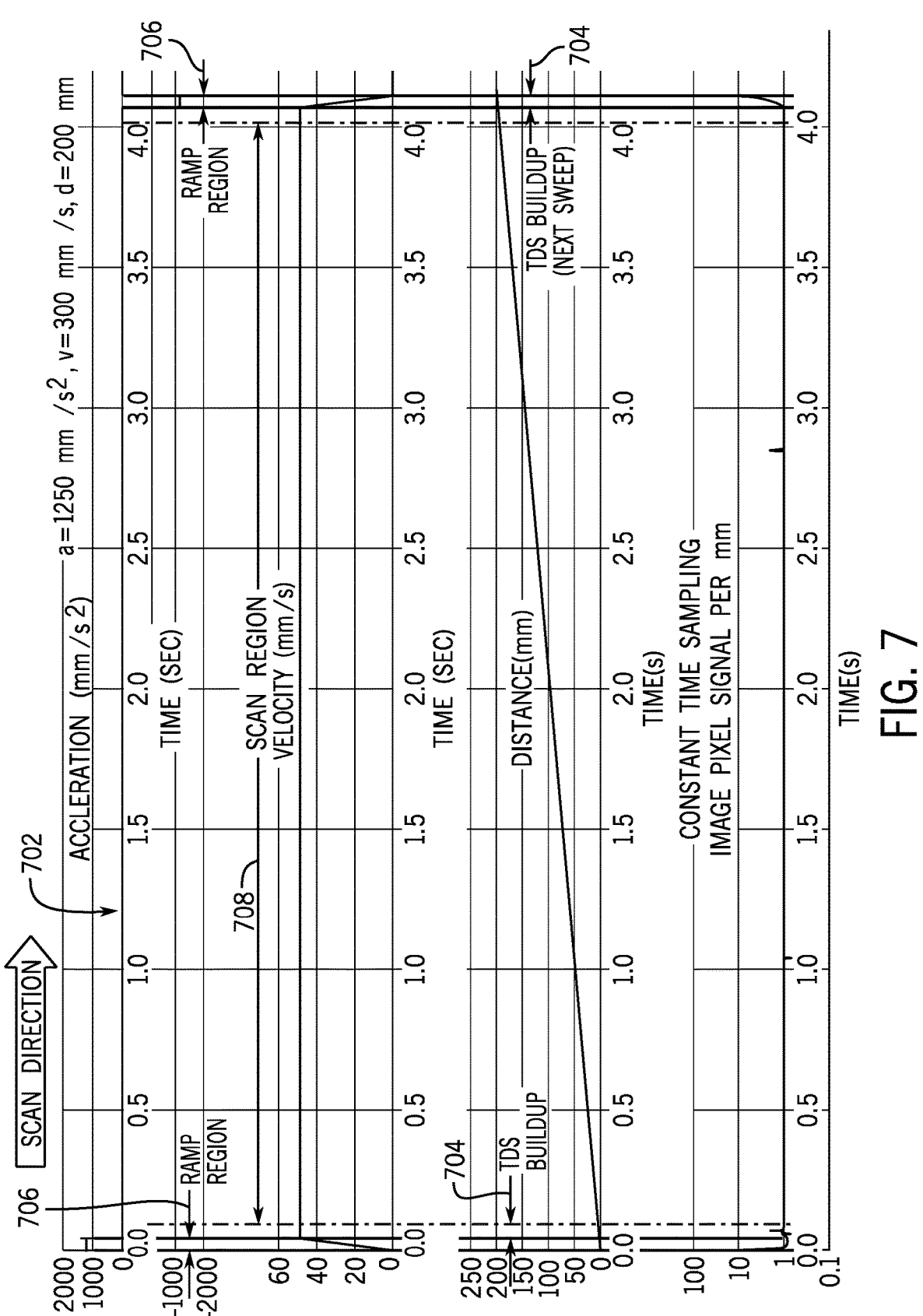
FIG. 7 illustrates plots of different parameters versus time for an example of a nominally flat-field image of one sweep of a transverse scan with a 32-column detector at a slow source speed using standard prior art TDS operation, i.e., constant time shifting.
Figure 8:
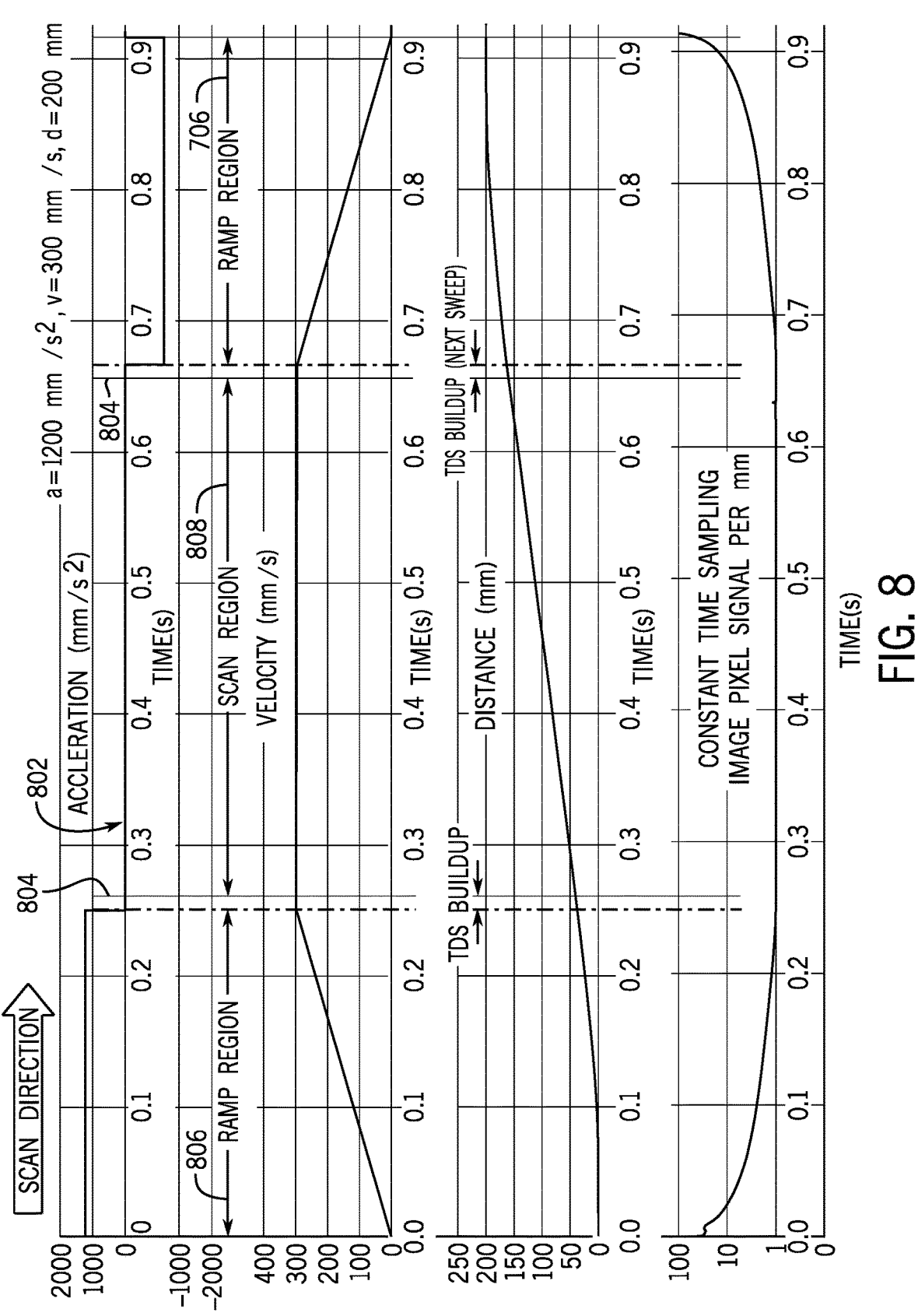
FIG. 8 illustrates plots of different parameters versus time for an example of a nominally flat-field image of one sweep of a transverse scan with a 32-column detector at a high source speed using standard prior art TDS operation, i.e., constant time shifting.
Figure 9:
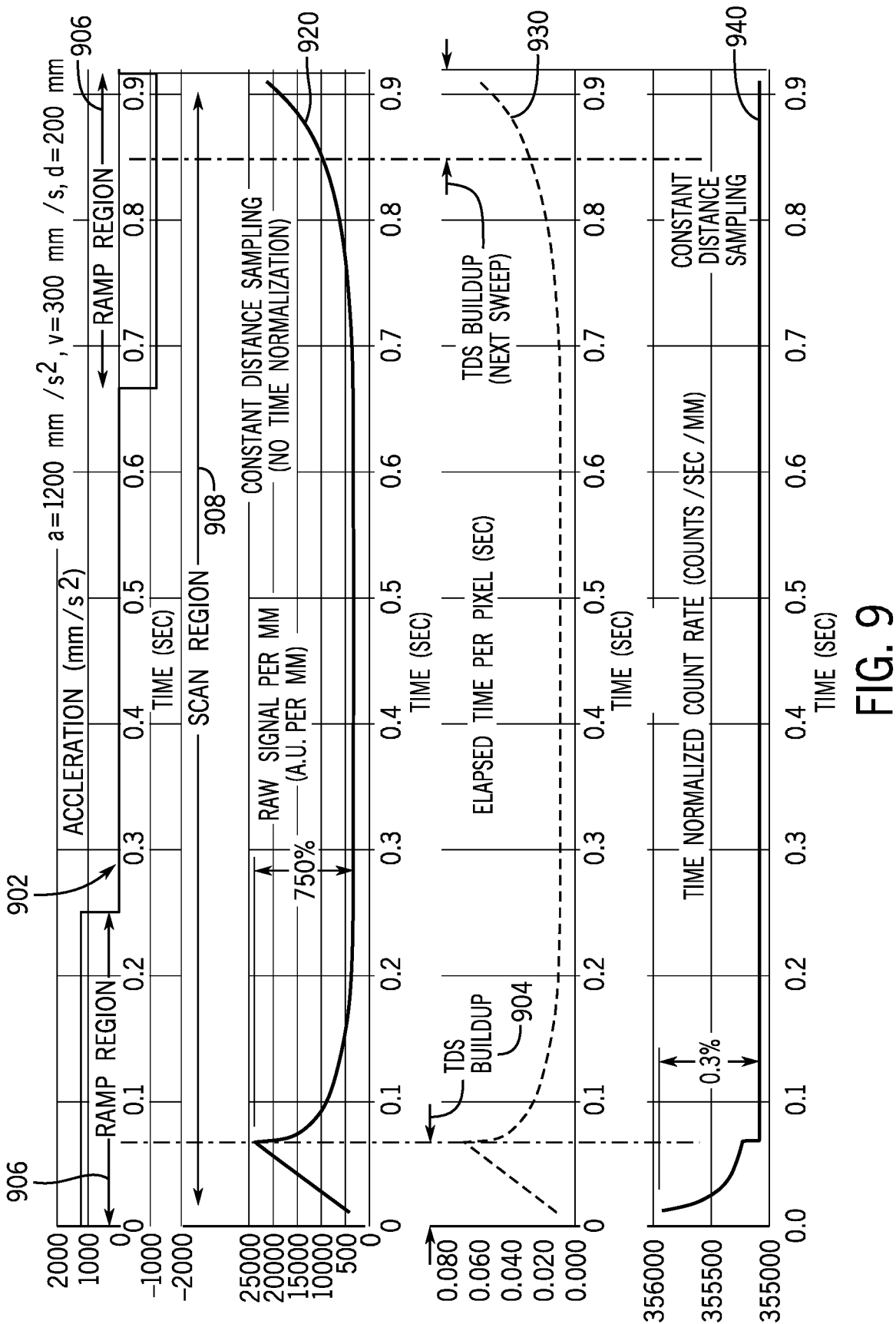
FIG. 9 illustrates plots of different parameters versus time for an example of a nominally flat-field image of one sweep of a transverse scan with a 32-column detector at a high source speed using an improved speed variable TDS operation, i.e., constant sampling distance TDS shifting, in accordance with an embodiment of the present technique.

With reference now to FIGS. 7 and 8, examples of nominally flat-field images of one sweep 702,802 of a transverse scan with a 32-column detector using standard prior art TDS operation, i.e., constant time shifting, are illustrated. In both figures, examples are shown where the acceleration and deceleration of the source 22 and detector 26 are constant at 1200 $mm/s^2$ and the full sweep width is 200 mm. FIG. 7 shows the case of where the constant scan velocity achieved for the TDS sweep 702 is 50 mm/s, which is a typical and modest scan speed for an anterior/posterior (AP) spine scan. In FIG. 8, the constant scan velocity achieved for the TDS sweep 802 is 300 mm/s, which is a desired speed for a body composition scan where the entire patient is scanned. In both examples, the sweep 702,802 has a short TDS buffer buildup 704,804 after the ramp or acceleration region or zone 706,806 ends. A symmetrically positioned TDS buffer 704,804 is required on the following sweep 702,802 when acceleration occurs in the opposite direction in a deceleration zone or region 706. The scan region 708,808 occurs where there is constant velocity and after the initial TDS buildup has occurred at constant velocity.

In FIG. 7 the upper three graphs show the acceleration-, velocity- and distance-travelled profiles at a scanning velocity of 50 mm/s. The entire 200-mm sweep 702 requires ~4.1 seconds. The ramp regions/zones 706 occurs during the acceleration and deceleration phases of motion and is only 0.042 seconds (~1 mm), which is ~2% of the entire sweep time. In standard TDS operation, the first 32 columns of data after the acceleration zone 706 ends and constant velocity is reached are also excluded from data analysis. This excludes another 0.053 seconds of data, which is an additional 1.25% of the sweep time. This 3.25% of excluded exposure time and 7 mm of scan distance, which is essentially wasted dose, is considered acceptable in bone densitometry. The bottom graph of FIG. 7 shows the image pixel signal per mm in the case of constant time sampling of a flat radiation field. The signal per mm is normalized by the values in the central region/scan region 708 of the plot where velocity is constant. Note that in the acceleration and deceleration regions/zones 706, there is a significant increase in the signal per mm—in this example, up to 20 to 30 times more x-rays per mm. Furthermore on the left side of the graph, the TDS build-up region 704 at the end of acceleration zone 706 demonstrates some non-constant signal per mm behavior.

At higher speeds, as in the graph of FIG. 8 showing profiles similar to FIG. 7 but where the desired scanning velocity is 300 mm/s, the ramp region/acceleration zone 806 takes 6 times longer (~0.25 sec) and the distance until achieving constant velocity is now ~37.5 mm. With the additional TDS buildup 804 distance of 2.7 mm after reaching full velocity and accounting for the subsequent TDS buffer/buildup 804 and deceleration region 806, approximately 80 mm of scan distance would be discarded. Since a body composition scan requires ~600 mm sweep width, extending the table width by 80 mm represents an additional ~13% wider table with its resulting increased cost and demands on the gantry for patient support. The bottom graph of FIG. 8, shows the image pixel signal per mm in the case of constant time sampling of a flat radiation field. The signal per mm is normalized by the values in the plot's central region/scan region 808, where velocity is constant. At higher final speeds relative to the acceleration rate, the extended region of non-constant signal per mm is evident, which is why quantitative DXA with conventional TDS operation would typically disregard data from this region.

An alternative and improved approach to prior art TDS sampling is provided by the speed variable TDS system and method of the current disclosure is shown in FIGS. 1 and 9-13. A motion controller 32 including a microprocessor 33 uses a motion program or profile 1002 such as stored in memory 41 of computer 40 to generate signals to a motor 35 to drive transverse motion of the detector 26 in a prescribed manner. With the knowledge of the distance the source 22 and detector 26 have travelled at all times during the performance of the sweep 902, such as via suitable sensors 1020 disposed on the C-arm 18 and/or the motor 35, the microprocessor 33 simultaneously generates each TDS shift strobe 1004,1104 to the detector 26 such that the distance traveled by the detector 26 between shift strobes 1004,1104 is always constant, i.e., a constant sampling distance TDS shift frequency, even during the variable speed periods occurring during the acceleration and deceleration zones 906 at each end of the sweep 902, excluding the TDS buffer or buildup zone 904 at each end of the sweep 902, greatly increasing the effective length of the scan region 908. The image pixel 1110 produced after N strobes 1004,1104 is thus composed of the summed x-rays from N constant-area sub-pixels 1108 and retains the advantageous property of TDS that its signal integration occurs along an essentially direct line between source 22 and a point of interest 310 in the imaged object 312.

Figure 10:
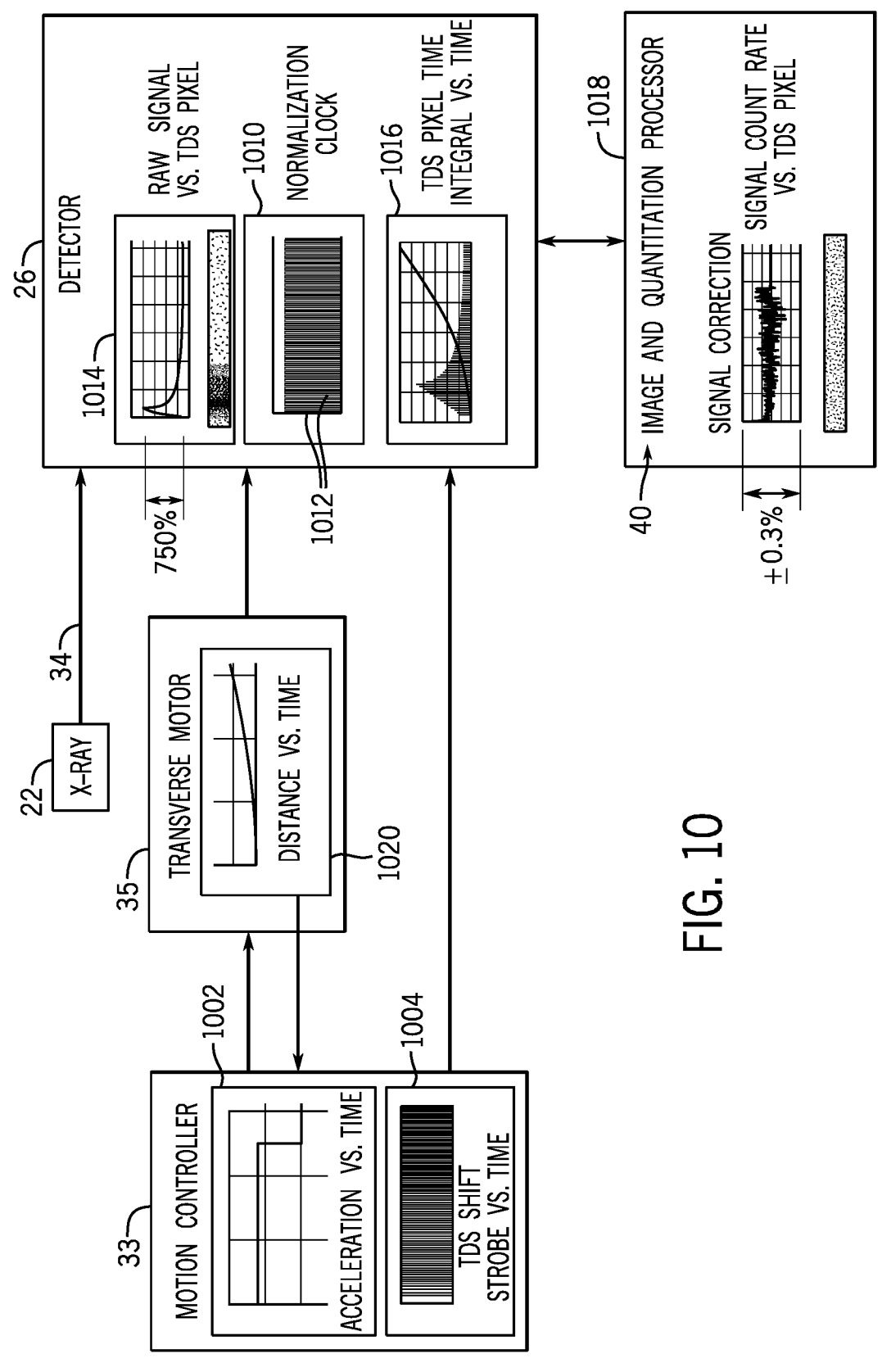
FIG. 10 is a flowchart illustrating the method of employing speed variable TDS operation, in accordance with an embodiment of the present technique.
Figure 11:
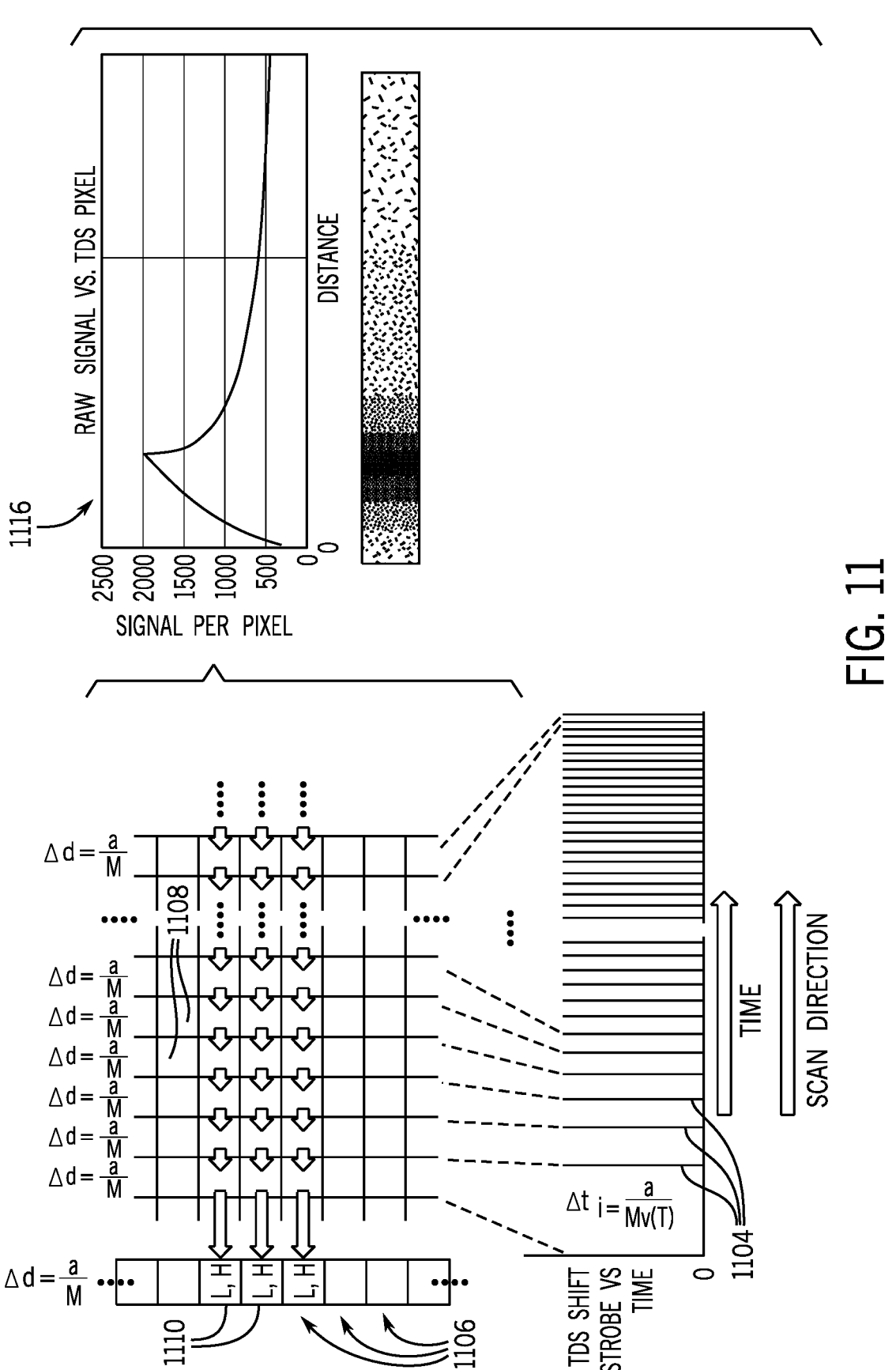
FIG. 11 is a schematic diagram depicting the effect of variable source speeds on speed variable TDS imaging procedures, in accordance with an embodiment of the present technique.
Figure 12:
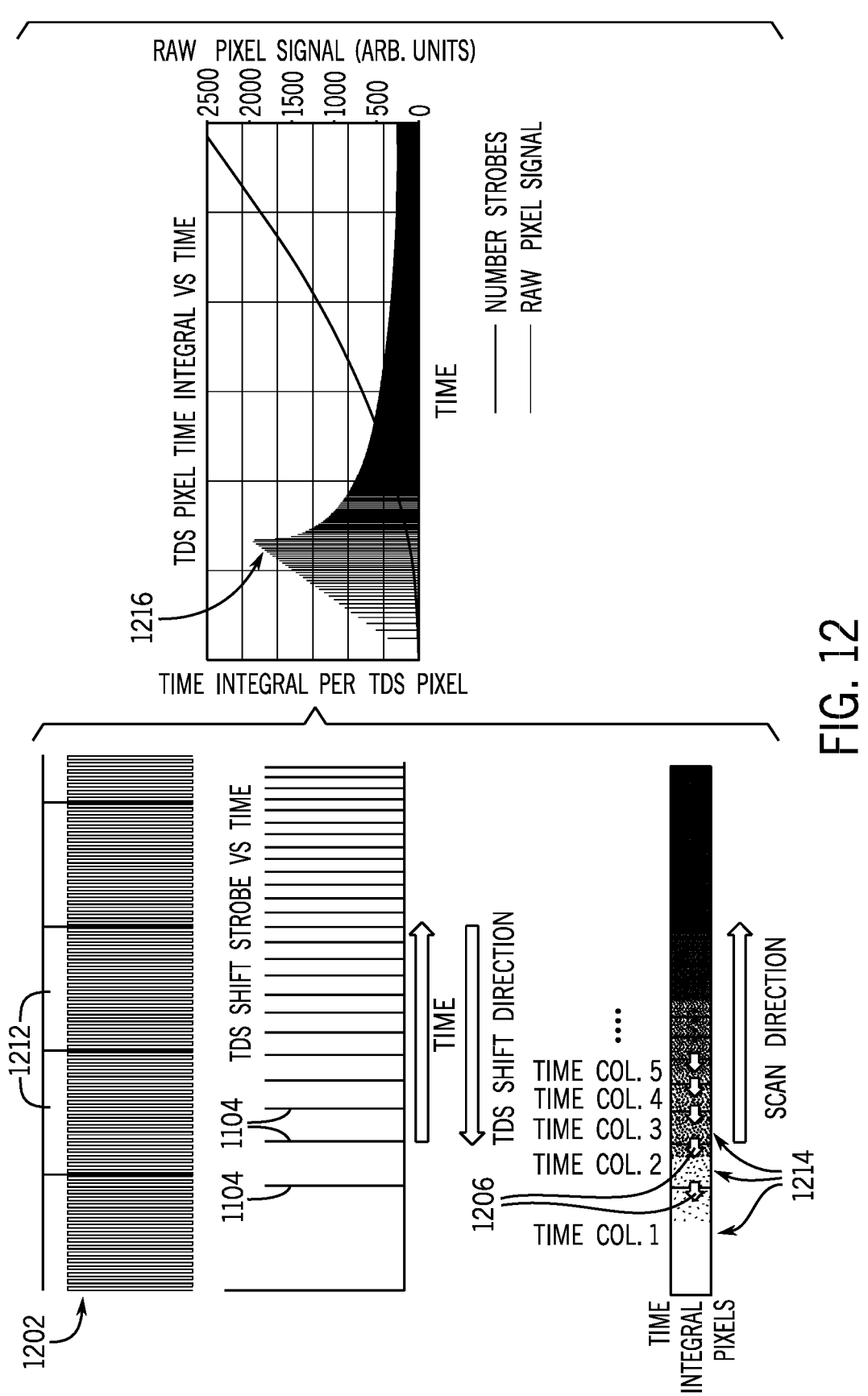
FIG. 12 is a schematic diagram depicting the operation of the normalization clock within the speed variable TDS imaging procedures, in accordance with an embodiment of the present technique.
Figure 13:
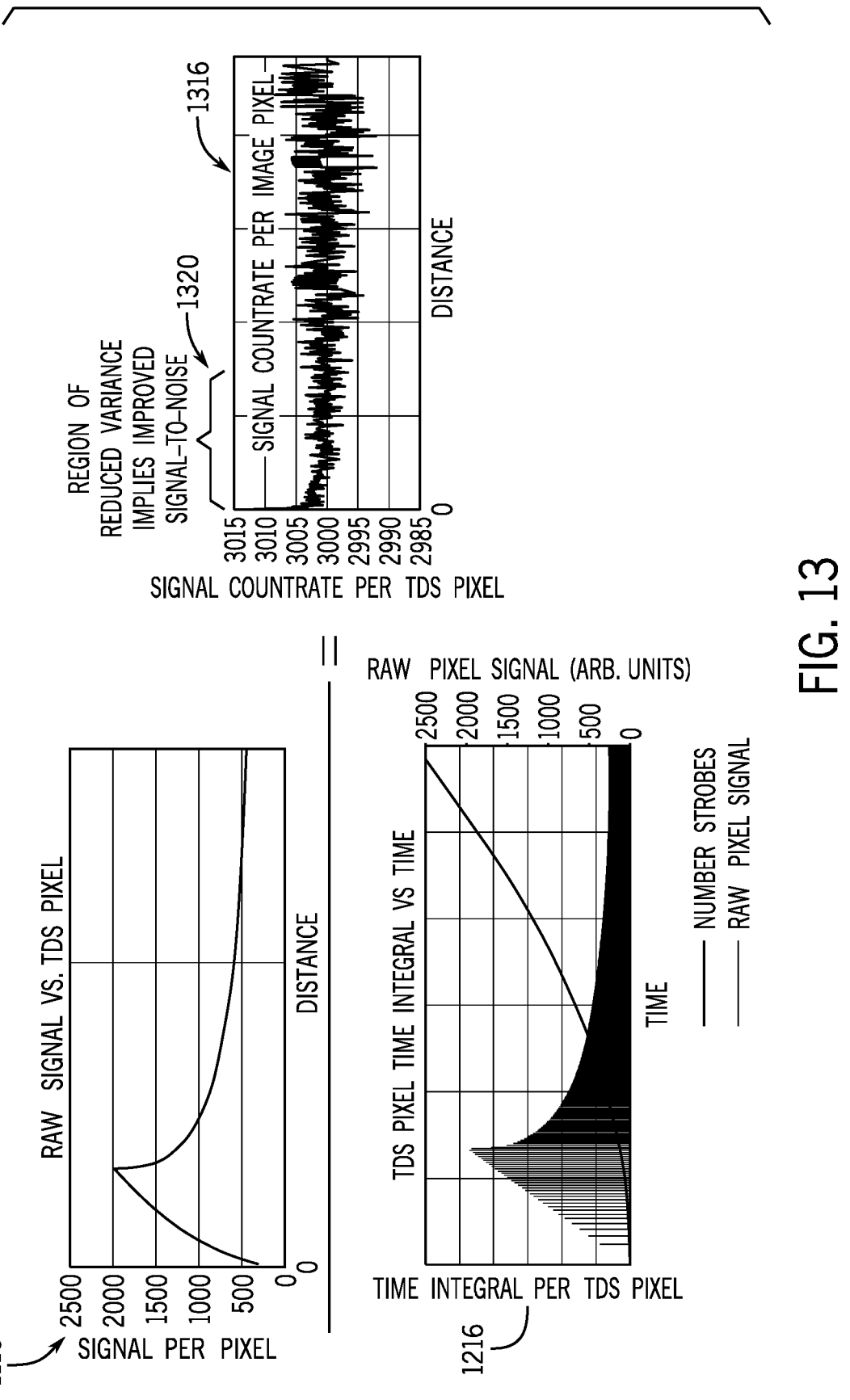
FIG. 13 is a schematic diagram depicting the Signal-to-Noise Ratio (SNR) enhancement in regions with slower motion within the speed variable TDS imaging procedures, in accordance with an embodiment of the present technique and the normalization process of the division of the raw signal per pixel by the integrated time per pixel.

In regions of constant speed during the sweep 902, i.e., in the scan region 908, the strobes 1004,1104 are issued with regular time intervals as in standard TDS acquisition. In regions of acceleration or deceleration (ramp regions 906), the strobes 1004,1104 may no longer be issued with regular time intervals as a result of the different times required to move the detector 26 the constant distance by the acceleration or deceleration of the motor 35 in the ramp zones 906 as defined by the program 1002, again, the constant sampling distance shift frequency. This implies that the recorded signal for each image pixel 1106,1108 will have a different duration of signal integration. Thus, each image pixel 1106, 1108 requires a time normalization 1018 so that signal intensities from pixel-to-pixel may be compared quantitively. As best shown in FIGS. 10-12, this normalizing time measurement, which can be performed in the detector 26, is performed by a free-running clock signal/normalization clock 1010,1202 having a significantly higher frequency than the highest anticipated frequency of the TDS shift strobes 1004,1104. The cycles 1012, of the normalization clock 1010, 1202 are counted in registers and are similarly shifted at 1206 as the TDS signal summation is shifted between sub-pixels 1108. After TDS strobes 1004, 1104 are issued across the entire sweep 902, the number or count 1214 of clock cycles 1012,1212 occurring during the entire shift sequence/sweep 902 is recorded along with each image pixel data line 1106. This clock cycle count 1214 serves as an estimate of the absolute time of signal integration 1016, 1116 for the pixel data line 1106. The raw signal 1014 of each sub-pixel 1108 along that line 1106 are subsequently corrected by division with their corresponding time estimate 1216. This normalization 1018 using the cycle count 1214 may occur in the detector 26 or upstream in the data acquisition controlling computer 40. Once time normalized, each image pixel 1316 now has a constant width and their count rates may be quantitatively compared to all other image pixels 1316 regardless of their location within the entire sweep 908.

During the TDS operation while register contents are being shifted to the neighboring pixels registers, there is a period of insensitivity where x-ray counting cannot be done. The duration of this insensitivity (or deadtime) must be considered in the time normalization 1018. If the time measurement is performed independently of the x-ray counting, for example by a clock and counter that is external to the detector 26, deadtime correction may be done by subtracting the known deadtime per shift or strobe 1004,1104, which is typically a constant time. Preferably, the clock cycles 1112 are counted in the same manner as x-rays/strobes 1004,1104 and thus experience identical deadtime. In this case, no explicit deadtime correction is required for the time measurement and signal normalization is simply the ratio of measured counts 1114 and measured clock strobes 1004, 1104. This is an important simplification since it reduces the need additional electronics and reduces the risk of not synchronizing the time count pixel to the image pixel.

Referring now to FIG. 9, the graph 920 of acceleration/time similar to FIGS. 7 and 8, as well as graphs of signal/mm, time/pixel and of time normalized count rate are shown for a sweep having constant acceleration/deceleration and with the high scan speeds shown in FIG. 8, but with the impact of variable sampling TDS and constant-distance sampling with time normalization employed in the performance of the scan sweep 902 by the detector 26 and the computer 40, as described previously with respect to FIGS. 1 and 9-13. The top plot 920 shows the raw signal per image pixel prior to time normalization vs time during a single sweep 902. The constant sampling distance shift frequency employed in the illustrated exemplary embodiment of the variable sampling TDS process in FIG. 11 is equivalent to the image pixel size, though the method can be employed with alternate distance values employed for the sampling employed, with an arbitrary but constant x-ray flux being assumed. The middle plot 930 shows the time-elapsed per image pixel, which has the same profile as the signal per pixel distribution in plot 920. The bottom plot 940 shows the final image pixel versus time after time normalization using the count 1114 of the signals from the normalization clock 1010 over the time for the sweep 902, which is just the division of the upper distribution in plot 920 by the middle distribution in plot 930. The raw signal distribution in plot 920 has a variation of 750% from the edge of the sweep 902, i.e., the point of the sweep 902 where the TDS buildup has been achieved, to the center of the sweep 902 where speed is constant. The time-normalized signal distribution in plot 940 has variation reduced to 0.3% in this example and only in the TDS buildup region 904, thus greatly enhancing the length of the sweep 902 over which image data can be collected and utilized in an imaging procedure. Furthermore, longer counting times for pixels in the acceleration regions result in higher x-ray counts per pixel, implying higher statistical precision in the count rate measurement, since the variance of the signal is proportional the sqrt (N), where N is the number of x-rays per image pixel. This reduced variance is equivalent to stating that the Signal-to-Noise Ratio (SNR) is enhanced in these regions 1320 with slower motion.

An alternate implementation of the variable time-sampling TDS system and method described herein is for dynamic modulation of scan speeds during patient scanning. The system and method of variable-speed TDS operation disclosed herein enables TDS operation in conditions where adjusting scan velocity in response to external signal intensity is desirable. For example, decreases in signal intensity occur when scanning denser regions of the object 310,312, meriting a dynamic lowering of scan speeds to increase the x-ray statistics per image pixel. Conversely, when signal intensity is high, increasing scan speed would reduce patient dose without a relative compromise to the statistical quality of image pixels. In an exemplary embodiment, as transmitted x-ray rates, i.e., external signal intensity, go down during scanning through thicker or highly attenuating material in the object 310,312, as sensed by the detector 26 and/or the computer 40, the computer 40 operate the motion controller 32 and the motor 35 to slow the movement of the C-arm 18, i.e., the source 22 and the detector 26, to increase the flux per imaging pixel. When TDS is used for data acquisition of the scans, constant signal-to-noise ratios may be achieved while maintaining a constant-sized imaging pixel by employing the variable-time sampling TDS system described previously.

In the event of inconsistent usages between this document and those documents so incorporated by reference, the usage in the incorporated reference(s) should be considered supplementary to that of this document; for irreconcilable inconsistencies, the usage in this document controls.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for performing a time delayed summation (TDS) in an imaging procedure for an object, the method comprising the steps of:
   providing an imaging device comprising:
      an X-ray source operative to transmit X-rays through an object, wherein the X-ray source is collimated to produce a diverging beam of radiation;
      a detector operative to receive the X-ray energy of the X-rays after having passed through the object;
      a processing system operably connected to the X-ray source and the detector, the processing system programmed to control movement of the X-ray source and the detector relative to the object, and to perform a time delayed summation (TDS) process to generate images from the X-ray energy received by the detector; and
      an electronic memory operably connected to the processing system and storing instructions for the operation of the processing system in performing imaging procedures;

determining a time delayed summation (TDS) shift frequency that varies with speed of the X-ray source and detector;
performing a scan of the object based on the speed-variable TDS shift frequency; and
generating an image of the object based on detected X-ray energy signals at the detector based on the scan.

2. The method of claim 1, wherein the step of determining the speed-variable TDS shift frequency comprises determining a constant sampling distance TDS shift frequency.

3. The method of claim 1, wherein the imaging device further comprises a normalization clock for generating a clock signal recorded in conjunction with the speed-variable TDS shift frequency.

4. The method of claim 1, wherein the electronic memory includes instructions for a sweep of the X-ray source and the detector over the object in performing the scan, the sweep including an acceleration zone, a constant speed zone and a deceleration zone, and wherein the step of performing the scan of the object comprises applying the speed-variable TDS shift frequency in each of the acceleration zone, the constant speed zone and the deceleration zone.

5. The method of claim 4, wherein the step of determining the speed-variable TDS shift frequency, comprises determining a constant sampling distance TDS shift frequency.

6. The method of claim 5, wherein the imaging device further comprises a normalization clock for generating a clock signal recorded in conjunction with the constant sampling distance TDS shift frequency, and wherein the method further comprises the step of time normalizing the detected X-ray energy signals with the recorded clock signal.

7. The method of claim 4, wherein the step of generating an image of the object based on detected X-ray energy signals based on the scan, comprises generating the image based on detected X-ray energy signals during each of the acceleration zone, the constant speed zone and the deceleration zone.

8. The method of claim 1, further comprising the step of dynamically adjusting scan velocity in response to external signal intensity.

9. The method of claim 1, wherein the electronic memory includes parameters for scan speed in relation to an intensity of the detected X-ray energy signals, and wherein the step of performing the scan of the object comprises adjusting the speed of the scan and the speed-variable TDS shift frequency.

10. The method of claim 9, wherein the step of determining the speed-variable TDS shift frequency comprises determining a constant sampling distance TDS shift frequency.

11. The method of claim 10, wherein the imaging device further comprises a normalization clock for generating a clock signal recorded in conjunction with the constant sampling distance TDS shift frequency, and wherein the method further comprises the step of time normalizing the detected X-ray energy signals with the recorded clock signal.

12. The method of claim 1, wherein the step of performing a scan of the object based on the speed-variable TDS shift frequency comprises performing a dual x-ray absorptiometry scan of the object.

13. The method of claim 1, wherein the step of performing a scan of the object based on the speed-variable TDS shift frequency comprises performing a bone mineral density scan of the object, a body composition scan of the object, or a combination thereof.

14. The method of claim 1, wherein the step of performing a scan of the object based on the speed-variable TDS shift frequency comprises performing bone densitometry scan of the object.

15. The method of claim 1, wherein the step of performing a scan of the object based on the speed-variable TDS shift frequency, comprises performing sequential transverse sweeps of the object with the X-ray source and the detector.

16. An imaging device comprising:

an X-ray source operative to transmit X-rays through an object, wherein the X-ray source is collimated to produce a diverging beam of radiation;

a detector operative to receive the X-ray energy of the X-rays after having passed through the object;

a processing system operably connected to the X-ray source and the detector, the processing system programmed to control movement of the X-ray source and the detector relative to the object, and to perform a time delayed summation (TDS) process to generate images from the X-ray energy received by the detector; and an electronic memory operably connected to the processing system and storing instructions for the operation of the processing system in performing imaging procedures;

wherein the processing system is configured to determine a time delayed summation (TDS) shift frequency that varies with speed of the X-ray source and detector and to perform a scan of the object based on the speed-variable TDS shift frequency, and wherein the electronic memory includes parameters for scan speed in relation to an intensity of the detected X-ray energy signals, and wherein the processing system is configured to adjust the speed of the scan and the speed-variable TDS shift frequency.

17. The imaging device of claim 16, further comprising a normalization clock for generating a clock signal recorded in conjunction with the constant sampling distance TDS shift frequency, and wherein the processing system is configured to determine a constant sampling distance TDS shift frequency.

18. The imaging device of claim 16, wherein the electronic memory includes instructions for a sweep of the X-ray source and the detector over the object in performing the scan, the sweep including an acceleration zone, a constant speed zone and a deceleration zone, and wherein the processing system is configured to adjust the speed-variable TDS shift frequency in each of the acceleration zone, the constant speed zone and the deceleration zone.

19. A medical imaging system comprising:

a multi-energy X-ray source operative to transmit X-rays through a patient, the X-ray source is collimated to produce a diverging beam of radiation;

a detector including a number of pixels arranged in at least one row and operative to receive the X-ray energy of the X-rays after having passed through the patient; and a processing system programmed to perform a scan of the patient based on a speed-variable time delay summation (TDS) frequency, to generate at least two images of a patient bone corresponding to the multi-energy levels of the multi-energy X-ray source, and to determine at least one of a patient body composition, a bone mineral density (BMD), and combinations thereof, based on the at least two images.

* * * * *